United States Patent [19]

Karpas

[11] Patent Number: 4,863,730
[45] Date of Patent: Sep. 5, 1989

[54] IMMUNOTHERAPY FOR AIDS PATIENTS

[75] Inventor: Abraham Karpas, Cambridge, United Kingdom

[73] Assignee: Cenfold Holdings, S.A., Panama City, Panama

[21] Appl. No.: 909,473

[22] Filed: Sep. 19, 1986

Related U.S. Application Data

[63] Continuation-in-part of Ser. No. 842,228, Mar. 21, 1986, Pat. No. 4,814,269.

[51] Int. Cl.⁴ .................. A61K 39/395; A61K 39/42; C07K 15/06; G01N 33/577
[52] U.S. Cl. .................................... 424/86; 424/85.8; 514/885; 436/547; 530/387; 530/403; 530/806
[58] Field of Search .......................... 424/86, 85, 85.8; 514/885, 2, 21; 436/507, 547, 548; 530/387, 806, 403

[56] References Cited

U.S. PATENT DOCUMENTS 4,617,379 10/1986 Dobkin et al. ...................... 530/388
4,639,513 1/1987 Hou et al. ........................... 530/387

FOREIGN PATENT DOCUMENTS

WO86/04613 8/1986 PCT Int'l Appl. .

OTHER PUBLICATIONS

Referee's report from the Proceedings of the National Academy of Sciences, U.S.A., on an article by Karpas, et al., "Effects of Passive Immunization in Patients with the AIDS-related Complex and Acquired Immune Deficiency Syndrome."
Stricker et al., "An AIDS-related Cytotoxic Autoantibody Reacts with a Specific Antigen on Stimulated CD4+ Cells", Nature, vol. 327, pp. 710–713, Jun. 1987.
Walker et al., "CD8+ Lymphocytes can Control HIV Infection in Vitro by Suppressing Virus Replication", Science, vol. 234, pp. 1563–1566, Dec. 1986.
Karpas et al., "Lytic Infection by British AIDS Virus and Development of Rapid Cell Test for Antiviral Antibodies", The Lancet, Sep. 28, 1985, pp. 695–697.

Primary Examiner—John Kight
Assistant Examiner—Nathan M. Nutter
Attorney, Agent, or Firm—Elliot M. Olstein

[57] ABSTRACT

An immunotherapy treatment for a patient infected with the virus giving rise to the acquired immune deficiency syndrome (AIDS) and resulting in a breakdown in the patient's immune response. In this treatment, a supply of plasma is derived from serum-positive individuals who carry the AIDS virus yet are free of the clinical symptons associated with AIDS or with any AIDS-related complex. The plasma supply is processed to provide a preparation rich in antibodies having neutralizing properties in respect to the AIDS virus, the processed plasma being free of red blood cells and other impurities. The processed plasma is transfused intravenously into the infected patient in a dosage which is safe and efficacious, and the transfusion procedure is repeated at spaced intervals of time until the deficiency in the immune response of the patient is substantially overcome.

16 Claims, No Drawings

IMMUNOTHERAPY FOR AIDS PATIENTS

RELATED APPLICATION

This application is a continuation-in-part of my co-pending U.S. application Ser. No. 842,228, filed Mar. 21, 1986 and now U.S. Pat. No. 4,814,269, whose entire disclosure is incorporated herein by reference.

BACKGROUND OF INVENTION

1. Field of Invention

The present invention relates generally to the treatment of immunodeficiency diseases, and in particular to an immunotherapy treatment for a patient suffering from the acquired immune deficiency syndrom (AIDS).

2. Status of Prior Art

An antigen is any substance which when introduced into a host animal or human provokes an immune response leading to acquired immunity. Where the immune response is deficient or malfunctions, this results in an immunodeficiency disorder.

An antigen may be a soluble substance (i.e., a bacterial toxin or serum protein) or it may be particulate in nature, such as a bacterial cell. In general, the greater the degree to which an antigen, in terms of its chemical composition and structure, is "foreign" to the individual being immunized, the greater its effectiveness in stimulating an immune response. A substance that acts as an antigen, whether a virus, a bacteria or a body cell, has on its surface and in some instances in its interior, a number of reactive sites or determinants. It is these determinants or epitopes that impart specificity to the immune response, for they constitute the sites that react with an antibody or a sensitized lymphocyte.

The immune response gives rise either to the formation of specific antibodies that circulate in the blood stream (humoral immunity) or to an increase in the number of specifically reactive cells, called lymphocytes (cell-medicated immunity), or to both. These specific antibodies and specialized lymphocytes both react to the antigen functioning as the immunizing agent. Immunity acquired in this manner makes it possible for the body to destroy or neutralize invading pathogenic microbes or other toxins. Accordingly, an individual's acquired immunity serves as his principal line of internal defense against pathogens.

Lymphocytes (white blood cells) are the precursor cells of both humoral and cell-mediated immunity. In the human body, one finds a pool of recirculating lymphocytes which flows from the blood system into the lymph nodes, the spleen and other tissues, and then back to the blood system by way of the major lymphatic channels. High concentrations of lymphocytes are found in the lymph nodes as well as at those sites where they are manufactured and processed: the bone marrow, the thymus and the spleen.

Stem cells existing in bone marrow have the potential to develop in a number of directions depending on various factors which influence their development. Thus, some develop into red blood cells and others into different types of white blood cells. The stem cells involved in immune responses differentiate into either B-type or T-type lymphocytes.

Thus, there are two main classes of lymphocytes involved in the immune system of humans and animals; namely, T-cells and B-cells. The first class, T-cells, are thymus derived, and are differentiated in this gland from stem cells. The thymus may be regarded as the master gland in the body's immune system. When they are present within this gland, the differentiating cells are terms "thymocytes." When processed to maturity, the T-cells then emerge from the thymus and circulate among the tissues, lymphatics and bloodstream and thereby form a large proportion of the recirculating small lymphocytes. Only about 20 percent of the recirculating pool is constituted by B-cells.

The T-cell class of lymphocytes have immunological specificity and are directly engaged as effector cells in the cell-mediated immune response. These effector cells behave as through they possess antibody-like molecules on their surface; and when they react with the inducing antigen, they bring about cytotoxic effects on cells, including those containing viral antigens. These effector cells are also responsible for graft rejection, for they react with foreign cells from the graft. Though T-cells do not secrete humoral antibodies, they are sometimes required for the stimulation of B-cells to enhance the production of antibodies. Moreover, T-cells can enlist the aid of macrophages in destroying pathogens.

The second class of lymphocytes, B-cells, are derived from bone marrow and are responsible for the humoral immunity response; for after contact with an antigen, they give rise to antibody-producing plasma cells. However, while they also develop from stem cells, B-type lymphocytes are capable of forming memory cells. These are long-lived, resting lymphocytes that have been so primed by prior contact with an antigen that upon renewed contact with the same antigen they produce a secondary immune response. This response is faster and more vigorous than the primary response and enables an individual who had previously been exposed to a pathogen to respond much more effectively in a subsequent encounter with this pathogen.

Microbiologists now recognize that T-cells, the first class of lymphocytes, can be divided into at least three subclasses termed "helper," "suppressor," and "killer" T-cells. "Helper" T-cells are those which act to promote a reaction, whereas "Suppressor" T-cells suppress a reaction. "Killer" T-cells are characterized by their "lysing" properties; that is, their ability to kill foreign cells.

The sub-classes for T-cells in human systems are described in greater detail by Chess and Schlossman in "Functional Analysis of Distinct Human T-Cell Subsets Bearing Unique Differentiation Antigens" (Contemporary Topics in Immunobiology—O. Stutman, Editor, Plenum Press 1977, Vol. 7, 363–379).

In the proper diagnosis or treatment of immunodeficiency disorders or conditions, the ability to correctly identify or suppress classes or sub-classes of lymphocytes is vital. See, for example, Aisenberg et al., The American Journal of Medicine 58:300—March 1975.

Thus, certain leukemias and lymphomas differ in their prognosis, depending on whether they are of the B-cell or T-cell origin; hence an evaluation of the disease prognosis makes it necessary to distinguish between these two classes of lymphocytes. In certain leukemias, excess T-cells are produced in an arrested stage of development, and proper diagnosis then depends on the ability to detect this imbalance.

The main concern of the present invention is with the acquired immune deficiency syndrome (AIDS) caused by a breakdown in the immunity response. This is attributed to the depletion of "helper" type T-cells which are killed by a human virus that is probably of African origin (See: Barre-Sinoussi et al., "Isolation of a T-lymphotropic Retrovirus From a Patient At Risk for Acquired Immune Deficiency Syndrome (AIDS)"—Science 1983; 220: 868–871).

The virus which causes AIDS, formerly identified as HTLV-III (human T-lymphotropic virus type III) or as LAV (lymphadenopathy-associated virus) or ARV (AIDS-related virus), has by a decision of the International Committee on Taxonomy of Virus designated this virus as HIV (human immunodeficiency virus).

AIDS is a recently recognized disease that is now evident in several parts of the world. Its overwhelming prevalence among homosexual men with multiple sexual partners, illegal intravenous drug abusers, hemophiliacs, blood transfusion recipients, and close heterosexual contacts of members of these high-risk groups strongly suggests that the disease spreads by the transmission of an infectious agent. The primary targets of affliction in the human body are specific subpopulations of T-cells. The severe immune deficiency of these patients results from an unusually low proportion of helper T-cells (T4) in their lymphocyte population, thereby reducing the availability of many T4 helper functions, among which is the production of antibodies by B-cells.

Those who suffer from AIDS become susceptible to a variety of rare illnesses. Most commonly found in AIDS patients are pneumocystis carinii pneumonia, a parasite-induced lung infection, and Kaposi's sarcoma, a rare form of cancer or tumor of the blood vessel walls.

Various types of antiviral drugs are presently undergoing tests, including the experimental drug azidothymidine (AZI). Currently there are no antiviral drugs that have been proven to cure AIDS or to ameliorate this condition. No drug for AIDS treatment has yet been accepted by the Federal Food and Drug Administration.

SUMMARY OF INVENTION

In view of the foregoing, the main object of this invention is to provide an immunotherapy treatment for a patient suffering from the acquired immune deficiency syndrome or the AIDS-related complex (ARC).

More particularly, an object of this invention is to provide an immunotherapy technique in which a patient infected with the AIDS virus and whose immunity response has been rendered deficient is supplied with antibodies which have a neutralizing effect on this virus, thereby arresting the progression of the deficiency to enable at least a partial recovery from the immune deficiency.

A significant advantage of the invention is that it makes no use of antiviral drugs and is therefore without adverse side effects encountered with such drugs.

Briefly stated, these objects are attained in an immunotherapy treatment for a patient infected with the virus giving rise to the acquired immune deficiency syndrome (AIDS) and resulting in a breakdown in the patient's immune response. In this treatment, a supply of plasma is derived from serum-positive individuals who carry the AIDS virus yet are free of the clinical symptoms associated with AIDS or with any AIDS-related complex. The plasma supply is processed to provide a preparation rich in antibodies having neutralizing properties in respect to the AIDS virus, the processed plasma being free of red blood cells and other impurities. The processed plasma is transfused intravenously into the infected patient in a dosage which is safe and efficacious, and the transfusion procedure is repeated at spaced intervals of time until the deficiency in the immune response of the patient is substantially overcome.

DESCRIPTION OF INVENTION

The AIDS Test Problem:

Essential to the present invention is an unambiguous and accurate test for the presence of the AIDS virus in an individual. The major mode of viral transmission of HIV apart from homosexual activity, is through blood and its products. It becomes important, therefore, to identify potential blood donors who are infected with the virus, and the only practical way to do so is to screen for circulating antibodies.

Enzyme-immuno assays, specifically termed enzyme-linked-immunosorbent assays (ELISA) are commonly used for the immunodiagnosis of viral infections and other microbial antigens. The ELISA diagnosis is based on the observations that some antigens can attach to a polystyrene plastic substrate and still maintain the full immunological capabilities, and that these antigens can be bonded to enzymes and the resulting complexes are still functional, both immunologically and enzymatically. It is the enzyme activity which is a measure of the quantity of antigens present in the test sample. This activity is indicated by a color change brought about by substrate hydrolysis which can be inspected visually.

As indicated in the article by Carlson et al., "Evaluation of Commercial AIDS Screening Test Kits," THE LANCET, 1985, i-1388, ELISA tests for the AIDS virus give an unacceptable level of false results.

In order, therefore, to provide a simple and accurate cell test system, we have developed a test (hereinafter referred to as the Karpas AIDS test) to detect antiviral antibodies with the use of a local isolate of the AIDS virus replicating in a Karpas test-cell line. This virus was obtained at Cambridge, England, from a male adult patient having an active AIDS condition. In the article by Karpas, "Unusual Virus Produced by Cultured Cells from a Patient with AIDS" (Mol. Biol. Med. 1983 1: 475–59), we have reported the expression of unusual virus particles in his cultured cells that were distinct from human T-leukaemic virus type 1 (adult T-cell leukaemia virus).

AIDS virus-infected and non-infected T-cells were used in our virological, serological, and electron microscopy studies. The latter showed a range of morphologically distinct virus-like particles, some of which resembled the unusual particles that we initially described in the above-identified Karpas article in the primary monocytoid cultures from the patient. They were clearly distinct from the enveloped forms but appeared to be developed and associated with the same cells that gave rise to the enveloped forms. In addition to these extracellular forms of virus, the infected cells contained large membrane-bound inclusions which were packed with virus particles.

These studies are reported in the Karpas et al. article, "Lytic Infection by British AIDS Virus and Development of Rapid Cell Test for Anti-viral Antibodies" (THE LANCET, Sept. 28, 1985). In FIG. 1 of this article, there is illustrated an ultra-thin section of part of the cytoplasm of C-LAV infected Karpas T-cells showing a membrane-bound inclusion body packed with virus particles (C-LAV refers to the Cambridge isolate of lymphadopathy AIDS virus).

Unlike other viral isolates in other human T-cell lines, the C-LAV isolate causes a complete cytolysis of the Karpas T-cells. However, since the Karpas T-cell line flourishes in vitro to practically unlimited quantities, a continuous supply of virus-infected cells can be generated.

The Screening Test System:

Approximately $10^5$ cells are placed in each well of a multi-well slide, air dried, and fixed for 10 min in acetone at room temperature. The slides contain three rows of wells. A drop of the test serum or plasma sample diluted 1 in 10 in saline or phosphate-buffered saline (PBS) is placed in each of two wells that contain virus-infected cells and in one well that contains non-infected cells. The preparation is incubated in a humidified chamber for 40–60 min at 37° C. then washed for 10 min in saline or PBS. A suspension of goat antibodies to human immunoglobulin (Sigma) tagged with horse radish peroxidase (HRP) is then added. In initial studies a parallel set of slides was treated with similar goat antibodies tagged with fluorescein. Thus, each serum/plasma sample was tested for antibodies in duplicate and by two methods. Each also included a control. Incubation in a humidified chamber was repeated and followed by washing for 10 min in saline or PBS. Fluorescein-stained preparations were examined with a fluorescence microscope while HRP-treated cells were stained with aminoethyl carbazole or equivalent substrates. The results of the immunoperoxidase (IP) reaction could be clearly distinguished by the naked eye and verified by examination under conventional low-power microscopy. Thus, FIG. 2 of the above-identified Karpas et al. article illustrates in two pictures the phase contrast of IP stained cells. One picture is that of virus-negative cells which show no color, while the second picture shows virus-positive cells which stain a reddish color and can be seen with the naked eye. Both preparations were incubated with serum containing anti-LAV antibodies.

The immunofluorescence (IF) and IP tests gave the same results. Table 1 below shows the striking difference in the incidence of LAV infection between London and Cambridge homosexuals tested.

TABLE 1

RESULTS OF SEROLOGICAL SCREENING

| Sera | | IF | IP | percent positive |
|---|---|---|---|---|
| Cambridge Sera: | | | | |
| Haemophiliacs | Factor VIII deficient | 6/27 | 6/27 | 22 |
| | Factor IX deficient | 0/10 | 1/10 | 0 |
| AIDS: drug addict | | 2/2 | 2/2 | 100 |
| Homosexuals (some promiscuous) | | 7/88 | 7/88 | 8 |
| London Sera: | | | | |
| (Westminster Hospital) Highly promiscuous homosexuals, some with AIDS-related complex (ARC) | | 61/226 | 61/226 | 27 |
| Swedish Sera: | | | | |
| Homosexuals with ARC | | 21/21 | 21/21 | 100 |

Table II below shows the results with 190 sera, which were also tested independently at the Public Health Laboratory Service, London, using the competitive radioimmunoassay (CRIA). (See: Mortimer et al., "Prevalence of Antibody to Human T lymphotropic Virus Type III by Risk Group and Area, United Kingdom 1978–84[ (British Med J. 1985; 290: 1176–79.) Unlike the high rate (12/190) of equivocal readings given with CRIA, clear and unambiguous results are given by our IP test.

TABLE II

SUMMARY OF THE SEROLOGICAL TESTS*

| PHLS | Cambridge | |
|---|---|---|
| | + | − |
| + | 47 | 0 |
| − | 3 | 128 |
| ± | 7 | 5 |

*A total of 190 sera from Addenbrooke's Hospital, Cambridge, and the Westminster Hospital, London, were tested independently both in Cambridge and at the Public Health Laboratory Service (PHLS), London.

Neutralization Tests:

In a preliminary study we tested sera-positive individuals for neutralizing antibodies to the AIDS virus. After 1 h incubation of 0.1 ml of serum samples with $10^4$ infectious C-LAV particles the Karpas T-cells were infected with the serum/virus mixture. Of the nine sera tested, we found that the two sera from AIDS patients did not block the lytic effect of the virus, whereas five out of seven sera from healthy antibody-positive homosexuals blocked the lytic effect for over 10 days.

Applications:

The restricted mode of transmission of the AIDS virus makes possible effective screening of carriers to check virus spread in the population. Since the commercially available virus-based ELISA test may give misleading results, our cell test system, which is simple and appears to be accurate, could provide the method of choice for large-scale screening.

The lytic effect of the AIDS virus on the Karpas human T-cells enables us to test for neutralizing antibodies also. The high levels of viral antigen which accumulate in the cells make it possible to monitor the results of IP staining with the naked eye. The incorporation in the test slides of wells with virus-negative cells allows the specificity of the reaction for each serum sample to be controlled separately. This ability to discriminate between antiviral and anticellular antibodies is very important in homosexuals and recipients of blood transfusions, who commonly have some anticellular antibodies.

Initially we used the IF test in parallel with the IP method, but since our current IP method using staphylococcus-A protein conjugated to HRP (Zymed) gives the same results as the IF test we now use only the IP method, which is simpler. The detection of positive reactions with the naked eye and confirmation with microscopy allows the elimination of the false readings associated with radioactivity or ELISA counters. No specialized expertise is required, nor any sophisticated equipment; a refrigerator and a conventional microscope are all that are needed. Any questionable result can easily be repeated, and in the unlikely event that IP remains questionable, similar slides can also be used in IF tests. The acetone fixation of the slides kills the virus and consequently the slides are entirely safe to handle. We have used satisfactory slides which had been stored at +4° C. for over three months.

The Karpas AIDS cell test is a simple and inexpensive method for large-scale screening of blood for anti-LAV antibodies and can give accurate results within 2 hours. Moreover, positive sera can be further monitored for neutralizing antibodies to the virus with the simple procedure described above. Thus, sera with high titres of neutralizing antibodies can be selected for immunotherapy treatment of AIDS patients.

Immunotherapy Treatment of AIDS:

Human blood is an aqueous solution of proteins, salts and small amounts of organic substances containing various types of cells and cell products in suspension. Blood drawn from the body may readily be separated by centrifugation into a fluid portion, termed the plasma, and a solid portion containing the "formed elements." These formed elements include the red and white blood cells as well as platelets which initiate the clotting process. Clotted or coagulated blood that has been centrifuged separates in a fluid, termed serum, and a solid containing the protein fibrin, a product of clotting.

The term "unprocessed plasma," as used herein, refers to the plasma as it is derived by separation from an individual's blood. The term "processed plasma," as used herein, refers to the plasma so obtained which has been processed in the manner to be later described so as to remove therefrom substantially all non-fluidic constituents other than certain antibodies.

An immunotherapy treatment in accordance with the invention requires the preparation of a specially processed plasma. A supply of unprocessed plasma is derived from serum-positive individuals who are free of any of the clinical symptoms associated with AIDS or ARC (AIDS Related Complex). The symptom-free individuals who are chosen as donors are those found to have a high titre of antibodies which are neutralizing to LAV (HIV). The selected individuals are put on a cell separator for the collection of approximately one liter of unprocessed plasma.

The plasma so obtained is transferred to sterile glass bottles, then left overnight in a refrigerator and spun the following day. This procedure enables the separation of residual red blood cells and coagulum that often form in stored plasma. The spun clear plasma is then brought to room temperature and 1 ml of $\beta$-propiolacton is added to 400 ml of plasma and stirred immediately and at frequent intervals during the next half hour. ($\beta$-propiolacton inactivates viruses before its hydrolysis.)

A sample of this processed plasma is taken in order to test for the presence of infectious LAV, and it is also screened for sterility. The processed plasma, if found acceptable, is then aliquoted and kept frozen.

Before use in patients, processed plasma from several donors are pooled for each intravenous transfusion to be administered. The reason for so pooling the processed plasma is the suspected antigenic drift which probably occurs in viruses of infected individuals who develop the clinical symptoms associated with AIDS or ARC. Pooled processed plasma should contain neutralizing antibodies to a wider range of epitopes or determinants in the envelope of the virus.

Each patient having an active case of AIDS was given 200 ml of such pooled plasma intravenously, a dosage found to be safe and efficacious. This transfusion was repeated at weekly intervals for at least four weeks and the patient was then tested to determine whether his immune deficiency had been arrested or diminished. The exact dosage is not critical, and a greater or less dosage may be given at weekly or more frequent intervals and the patient's condition monitored to determine the efficacy of the treatment.

While there has been shown a preferred immunotherapy technique for treating patients infected with the AIDS virus, essentially the same technique is applicable to patients suffering from other immunodeficiency disorders.

Therapeutic Applications for Polyclonal and Monoclonal Antibodies

Normally, antibodies are synthesized by lymphoid cells derived from B lymphocytes of bone marrow. The great diversity of antibody specificities results from immunoglobulin molecules possessing many structural features in common. Individual antibody molecules of heterogeneous binding specificity differ in their detailed amino acid sequences. Hence, even antibodies having the same specificity are usually a mixture of immunoglobulins having different amino acid sequences, although such sequences may be substantially homologous. The terms "antibody" and "immunoglobulin" are interchangeable.

Individual lymphocytes produce immunoglobulin of a single amino acid sequence. Lymphocytes cannot be directly cultured to produce their specific antibody. However, Kohler and Milstein (Nature: 256,495 (1975)) demonstrated for the first time that a process of somatic cell fusion, specifically between a lymphocyte and a myeloma cell, could yield hybrid cells which grow in culture and produce a specific antibody. Myleoma cells are lymphocyte tumor cells which, depending upon the cell strain, frequently produce an antibody themselves, although some "non-producing" strains are known. Since this seminal work, much effort has been directed to the production of various hybrid cells resulting from the fusion of a lymphocyte and a myeloma cell. These are called "hybridomas."

Hybridoma production is an in vitro hybridization process. In this process, the genetic materials of both these cells are joined to create a hybrid cell that contains desirable characteristics from both predecessors, specific homogeneous antibody production and immortality.

In the fusion procedure, spleen lymphocytes from an animal immunized against a chosen antigen are fused with myeloma cells, and the resulting hybridomas are then dispersed in a series of separate culture tubes or microtitre plate wells to screen for cultures producing a desired antibody. Positive cultures are further diluted to obtain colonies arising from a single cell, these being designated clones. The clones are again screened for production of the desired antibody. An antibody derived from a cloned hybridoma is therefore termed "monoclonal."

Monoclonal antibodies are highly specific and are effective only against a single antigen. Moreover, in contrast to conventional antibody preparations which include different antibodies directed against different sets of determinants on the same antigen, monoclonal antibodies are directed only against a single determinant on the antigen. Monoclonal antibodies are useful in improving the selectivity and specificity of diagnostic and analytic assay methods using antigen-antibody binding.

The following articles deal with various aspects of monoclonal antibody production: (a) Reinherz et al.—Journal Immunol. 124: 1943–1948 (1980); (b) Kung et al.—Transp. Proc. XII (Supp. 1): 151–146 (1980); and (c) Kung et al., Int. J. Immunopharmacol. 3: 175–181 (1981). The following articles deal with monoclonal antibodies in clinical medicine: (d) Reinherz et al.—Proc. Natl. Acad. Sci. USA 77: 1588–1592 (1982); (e) McMichael et al.—Immunol. Today 3: 56–60 (1980); and (I) Raeman et al.—Clin. Exp. Immunol. 45: 475–479 (1981).

The production of monoclonal antibodies by the hybridoma technique represents a major innovation in clinical immunology. It is now recognized that monoclonal antibodies possess the potential for the production of a highly specific therapeutic agent which can be reproducibly manufactured to clinical standards of purity and consistency. Thus, monoclonal antibodies have been used in vivo as an immunosuppressive drug for patients undergoing acute rejection of histocompatible renal grafts. Monoclonal antibodies are also being developed for the treatment of leukemia in a procedure in which leukemic-reactive monoclonal antibodies are used to treat patients directly.

In order to produce monoclonal antibodies capable of functioning as a therapeutic agent in the treatment of AIDS, one must provide antibodies capable of killing or neutralizing the AIDS virus.

It is now known that human cells have surface antigenic structures similar to those of mice. To produce a hybridoma cell line of AIDS-virus reactive monoclonal antibodies, the following is the preferred procedure:

Single spleen suspensions from mice immunized with respect to the AIDS virus and therefore having antibodies which neutralize this virus are mixed with myeloma cells and fused by the addition of polyethylene glycol and dimethylsulfoxide to final concentrations of 35% and 5%, respectively. After this fusion, aliquots of washed cells are distributed into tissue culture cells and these are incubated for a week or more in a HAT medium (hypoxathine, aminopterin, thymidine).

The supernatant fluid from each cell showing hybridoma growth is screened against a panel of target cells in order to identify the supernatant fluids containing the desired antibody. The screening technique employed for this purpose may be an indirect immuno fluorescent assay, using a flow cytometer for analysis. Cultures exhibiting the desired reactive properties are cloned and recloned several times by a limiting dilution method to insure that each reactive culture is ultimately derived from a single hybridoma cell, and also to ensure that genetic stability has been attained.

Then the monoclonal antibodies are purified using known techniques for this purpose and reconstituted to provide a stock of antibody solution which is a 3:3 to 1 dilution of acetic fluid in a phosphate buffer.

A preferred technique for producing monoclonal antibodies capable of neutralizing the AIDS virus in an infected human patient is to obtain by way of a spleen biopsy from a human donor who carries the AIDS virus but is free of the clinical symptoms of this disease, a spleen sample. This is then fused with human mycloma cells, the technique otherwise being along the lines described above in connection with immunized mice. Or instead of a spleen sample, peripheral blood may be taken from the human donor.

Some advantages may be gained by developing polyclonal antibodies for the treatment of AIDS which are effective against more than one antigen. In this case, one makes use of peripheral blood derived from a human donor who carries the AIDS virus but is free of the clinical symptoms of this disease so that the blood includes neutralizing antibodies. The technique for producing polyclonal antibodies is well known in the art and therefore will not be described herein.

I claim:

1. An immunotherapy technique for the treatment of a patient infected with a virus resulting in an immunodeficiency disease, said technique comprising the steps of:

A. deriving a supply of plasma from serum-positive individuals who carry said virus yet are free of clinical symptoms associated therewith;

B. processing the plasma so derived to provide a preparation having a high titre of antibodies possessing neutralizing properties in respect to said virus, the processed virus being free of red blood cells and other impurities;

C. intravenously transfusing into the infected patient the processed plasma in a dosage which is safe and effective; and D. repeating the transfusion procedure at spaced intervals of time until the deficiency in the patient's immune system is substantially overcome.

2. A technique as set forth in claim 1, wherein said virus is HIV.

3. A technique as set forth in claim 1, wherein a screening test is employed to distinguish between said individuals and those who exhibit symptoms associated with the disease so that the plasma is derived exclusively from individuals who are free of said symptoms.

4. An immunotherapy technique as set forth in claim 1, wherein said transfusion dosage is about 200 ml.

5. An immunotherapy technique as set forth in claim 4, in which said transfusion is repeated at weekly intervals for at least 4 weeks.

6. An immunotherapy technique as set forth in claim 1, wherein the processed plasma is derived from several individuals and is pooled prior to transfusion.

7. A technique as set forth in claim 1, wherein the plasma is processed by storing it in a refrigerator for several hours, and then spinning it to separate the residual blood cells and coagulum from the stored plasma.

8. A preparation for the treatment of patients infected with a virus resulting in the acquired immune deficiency syndrome (AIDS), said preparation being constituted by plasma derived from serum-positive individuals who carry said virus yet are free from the clinical symptoms associated with AIDS, said plasma having been processed to exclude therefrom substantially all non-fluid constituents other than antibodies which are neutralizing with respect to said virus.

9. A preparation as set forth in claim 8, wherein the preparation is the processed plasma pooled from different individuals.

10. A process for treating a patient infected with a virus resulting in an immuno-deficiency disease, comprising:
    intraveneously infusing into the patient an effective amount of neutralizing antibodies to said virus resulting in an immuno-deficiency disease.

11. The process of claim 10 wherein said virus is HIV and said disease is AIDS.

12. The process of claim 11 wherein said antibodies were derived from at least one serum positive individual who carries said virus and is free of clinical symptoms associated therewith.

13. The process of claim 12 wherein said antibodies were derived from the plasma of at least one individual treated by removal of red blood cells and coagulum and invactivation of viruses.

14. The process of claim 13 wherein said antibodies were obtained by pooling of treated plasma from a plurality of individuals.

15. A composition for treating patients infected with AIDS comprising:
    an effective amount of neutralizing antibodies to HIV, essentially free of cellular matter.

16. The composition of claim 15 wherein said antibodies were derived from at least one serum positive individual who carries said virus and is free of clinical symptoms associated therewith.

* * * * *